United States Patent [19]

Webster

[11] Patent Number: 5,380,339
[45] Date of Patent: Jan. 10, 1995

[54] PARASITE REMOVER

[76] Inventor: Robert M. Webster, 195 Green Valley Rd., Fairburn, Ga. 30213

[21] Appl. No.: 123,135

[22] Filed: Sep. 17, 1993

Related U.S. Application Data

[63] Continuation-in-part of Ser. No. 854,211, Mar. 20, 1992, Pat. No. 5,246,449.

[51] Int. Cl.⁶ ............................................. A45D 26/00
[52] U.S. Cl. ................................... 606/131; 606/210
[58] Field of Search ....................... 254/28, 25, 18; 294/99.2; 227/63; 606/205–211, 131, 133

[56] References Cited

U.S. PATENT DOCUMENTS

| | | | |
|---|---|---|---|
| 262,875 | 8/1582 | Wills | 606/210 |
| 590,760 | 2/1897 | Heath . | |
| 1,138,881 | 5/1915 | McFarland . | |
| 1,657,497 | 1/1928 | Cichon . | |
| 2,033,050 | 3/1936 | Pankonin | 254/28 |
| 2,277,587 | 3/1942 | Gustafson | 254/28 |
| 2,431,922 | 12/1947 | Curtiss | 254/28 |
| 3,060,442 | 10/1962 | Tomek | 1/49.8 |
| 4,213,460 | 7/1980 | Weiner . | |
| 4,219,187 | 8/1980 | Brumfield | 254/28 |
| 4,442,837 | 4/1984 | Keatley . | |
| 4,487,394 | 12/1984 | Rothfuss et al. | 254/28 |
| 4,674,727 | 6/1987 | McAlister | 254/28 |
| 4,805,876 | 2/1989 | Blake et al. | 254/28 |
| 4,930,749 | 6/1990 | Lawrence | 254/28 |
| 4,938,764 | 7/1990 | Glaberson | 606/131 |
| 4,939,959 | 7/1990 | Rokita | 81/44 |
| 4,976,718 | 12/1990 | Daniell | 606/131 |
| 5,085,404 | 2/1992 | Thieleke et al. | 254/28 |
| 5,116,347 | 5/1992 | Butler | 606/210 |

Primary Examiner—Stephen C. Pellegrino
Assistant Examiner—Glenn K. Dewson
Attorney, Agent, or Firm—Hopkins & Thomas

[57] ABSTRACT

A first embodiment of a novel parasite remover has a holding plate and an engagement plate for attachment to pivoting arms of a staple remover. The holding plate has a slot for insertion between a parasite body and the skin of a host to which the parasite has attached itself. The engagement plate has a pair of curved prongs spaced apart to define a slot therebetween for straddling the parasite mouth which is inserted into the host skin. As the pivoting arms of the staple remover are moved together, the curved prongs engage the parasite body and extract the parasite from the host skin. A second embodiment has a handle arm and a lever arm which are pivotally mounted together. As a result, the lever arm has a prying end pivotal with respect to a trigger end. The handle arm engages and lifts a parasite away from the host skin. On the lever arm, the prying end presses the host skin in a direction substantially normal to the host skin upon application of user force at the trigger end. The second embodiment can be provided in a pocket knife assembly. Third embodiment has a pair of juxtaposed wedge shaped fingers defining a slot in a plate, the plate being carried at one end of an arm of tweezers so that one arm of the tweezer urges the body of the parasite between the fingers toward the thicker portion of the fingers.

6 Claims, 3 Drawing Sheets

PARASITE REMOVER

This is a continuation-in-part of application Ser. No. 07/854,211 filed Mar. 20, 1992 now U.S. Pat. No. 5,246,449.

FIELD OF THE INVENTION

The present invention relates in general to instruments for removing a parasite from a host, such as a human being or other animal, and more particularly, to an inexpensive and efficient parasite remover for readily and safely removing parasites.

BACKGROUND OF THE INVENTION

When a parasite is to be removed from the skin of a host, such as a human being or other animal, an extremely important consideration is preventing infection of the host and the person removing the parasite by infectious agents within the parasite. Rocky Mountain Spotted Fever and Lyme Disease are two common examples of infectious agents which can be transmitted by the parasite. The problems associated with preventing infection are common to many different types of parasites. Consequently, the discussion of these problems hereafter as they relate to ticks, for example, will be instructive as to all parasites generally and will serve to illustrate the precautions necessary to guard against infection by the many other types parasites.

After a tick has attached itself to the skin of a host, the tick secretes an adherent cement to secure itself to the host's skin, but several hours may elapse before infectious agents are transmitted into the host. During this time, if the tick can be removed, the chances of infection are greatly reduced. Therefore, removal of the tick needs to be done quickly, and any means for so doing should be readily available and easy to use.

Complete removal of the tick from the host is also critical. It is necessary, therefore, in addition to removing the tick from the host's skin, to remove the tick mouth parts imbedded in the skin and may remove the adherent cement secreted adjacent the mouth for attaching the tick to the skin. Removal of the body of the tick, the mouth of the tick, and the adherent cement is the safest way to prevent infection. In addition, removal of the tick should be methodically accomplished without irritating the tick. Squeezing, crushing, or bending the tick during removal may irritate the tick, thereby stimulating the tick to undesirably transmit infectious agents into the host, onto the host's skin, and/or onto the hands of the person removing the tick.

Prior art methods and apparatus for removing ticks from a host are shown in U.S. Pat. Nos. 4,213,460, 4,442,837, 4,938,764, and 4,976,718, which are incorporated by reference as if set forth in full hereinbelow. However, the parasite removers described in the foregoing prior art patents are undesirably elaborate and complex in design, and therefore are generally expensive. Furthermore, the prior art removers often squeeze, crush, bend, or otherwise damage parasites as the parasites are pulled from the host's skin, thereby irritating the tick to secrete infectious fluids and/or leaving tick mouth parts imbedded in the skin.

Thus, a need exists for a parasite remover which is simple in design, which is inexpensive to manufacture, and which can completely remove a parasite from a host in an efficient, nonirritating manner, thereby preventing infection of both the host and the person removing the parasite.

SUMMARY OF THE INVENTION

Briefly described, the present invention is a parasite remover for removing a parasite from the skin of a host by applying a resistance force to the host skin while extracting the parasite in a direction generally normal, or perpendicular, to the host skin. In essence, the parasite remover has an engaging means and a resisting means, which all can take various configurations.

The engaging means is inserted between the body of the parasite and the host skin and engages the portion of the parasite body substantially near the parasite mouth, which protrudes from the parasite body into the host skin. Furthermore, the engaging means applies upward force to the parasite body in a direction generally normal, or perpendicular, to the surface of the host skin. Removing the parasite perpendicularly from the surface of the host skin helps prevent bending or twisting the parasite mouth, which could possibly irritate the parasite.

The resisting means resists movement of the host skin toward the parasite as the parasite is pulled perpendicularly away from the host skin and as the parasite mouth is extracted from the host skin. The resisting means helps prevent the parasite mouth from pulling, or tugging, the host skin, thus allowing for easy extraction of the parasite mouth from the host skin.

In a sense, the present invention can be viewed as a broad method. In accordance with the methodology, a parasite is initially engaged between the parasite body and the host skin. The parasite body is then forced in a direction generally normal to and away from the host skin. Moreover, movement of the host skin toward the parasite is resisted as the parasite is forced away from the host skin.

In a first embodiment of the present invention, the resisting means has a holding plate to be inserted between the parasite body and the host skin. The holding plate has an aperture for substantially surrounding the parasite mouth near the surface of the host skin. A slot is provided as a throughway to permit the parasite mouth to be slid easily into the aperture. The holding plate resists movement of the host skin toward the parasite as the parasite is forced from the skin surface and also helps to extract the parasite mouth in a direction generally normal to the surface of the host skin.

The engaging means of tile first embodiment comprises a pair of spaced parallel prongs having distal ends defining a slot for insertion about the parasite mouth and between the parasite body and the host skin. The prongs exert force against the parasite body in a direction generally normal to and away from the host skin.

A moving means may be provided in the first embodiment. In essence, the moving means moves the spaced parallel prongs of the engaging means toward the holding plate to a position where the distal ends of said prongs are positioned between the holding plate and the parasite body.

During the operation of the first embodiment, the aperture of the holding plate is initially placed around the parasite mouth between the parasite body and the host skin. The engagement plate is then moved toward the holding plate. As the engagement plate moves toward the holding plate, the distal ends of the engagement plate prongs move along a curved path between the parasite body and the holding plate with the prongs straddling the parasite mouth. As the prongs engage the parasite body, the portions of the prongs straddling the parasite mouth move away from the host skin due to the prong curvature, thereby applying upward force to the parasite body in a direction generally normal to the host skin. Significantly, the holding plate stabilizes the host skin as the engagement plate pulls the parasite from the host skin, and the distal ends of the engagement plate prongs ensure that the adherent cement secreted by the parasite is removed, in large part, along with the body and mouth of the parasite.

In accordance with an additional feature of the first embodiment, both the holding plate and the engagement plate can be adapted for mounting at opposed ends of a commercially available staple remover or other similar device.

In a second embodiment of the present invention, a handle arm is configured to engage and lift the parasite away from the host skin. A lever arm is pivotally mounted to the handle arm. The lever arm has a prying end pivotal with respect to a trigger end. The prying end presses against the host skin in a direction substantially normal to the host skin upon application of user force at the trigger end.

To remove a parasite with the second embodiment, a user inserts the prying end between the parasite body and the host skin. Fork prongs may be provided at the distal end of the handle arm so, as to straddle the parasite mouth. The trigger arm is moved toward the handle arm, causing the prying arm to pivot away from the handle arm and engage the host skin near the parasite mouth. The engagement of the prying arm against the host skin causes the handle arm to lift up on the prongs and thereby apply upward force to the parasite body in a direction generally normal to the surface of the host skin, while the prying arm resists upward movement of the host skin.

In accordance with an additional feature of the second embodiment, a conventional pocket knife assembly can be provided to house the handle arm and the lever arm.

The third embodiment of the present invention discloses tweezers, one arm of which carries a wedge shape engagement plate which protrudes toward the other arm so that the other arm can sweep over the plate. The plate is bifurcated, having different length fingers, between which the parasite is received and lifted from the skin of the host, as the body of the parasite is urged toward the other arm.

Accordingly, it is an object of the present invention to provide a parasite remover for removing parasites from a host with reduced risk of infection of the host or the person removing the parasite.

Another object of the present invention is to provide a parasite remover which removes a parasite effectively from the host skin, including removing the parasite mouth parts and may remove the adherent cement secreted by the parasite.

Another object of the present invention is to provide a parasite remover that is simple in design, inexpensive to manufacture, and easy to use.

Another object of the present invention is to provide a parasite remover that is efficient in operation and durable in structure.

Another object of the present invention is to provide a parasite remover that removes a parasite from a host without irritating the parasite.

Other objects, features, and advantages of the present invention will become apparent from the following specification, when read in conjunction with the accompanying drawings.

BRIEF DESCRIPTION OF THE DRAWINGS

The present invention, as defined in the claims, can be better understood with reference to the following drawings. The drawings are not necessarily to scale, emphasis instead being placed upon clearing illustrating the principles of the present invention.

DETAILED DESCRIPTION OF THE PREFERRED EMBODIMENT

Figure 1:
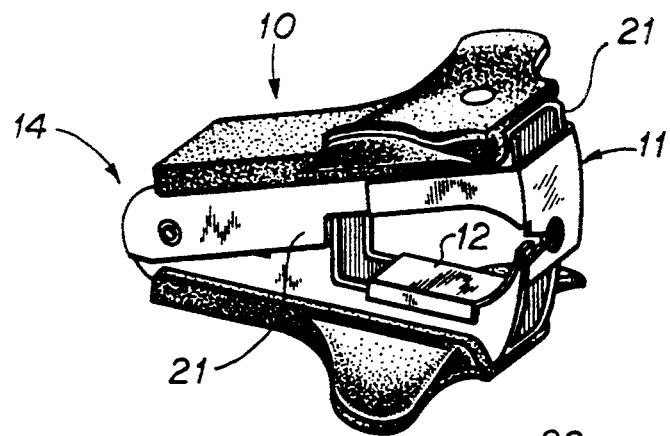
FIG. 1 is a perspective view of a first embodiment of the novel parasite remover in accordance with the present invention.
Figure 2:
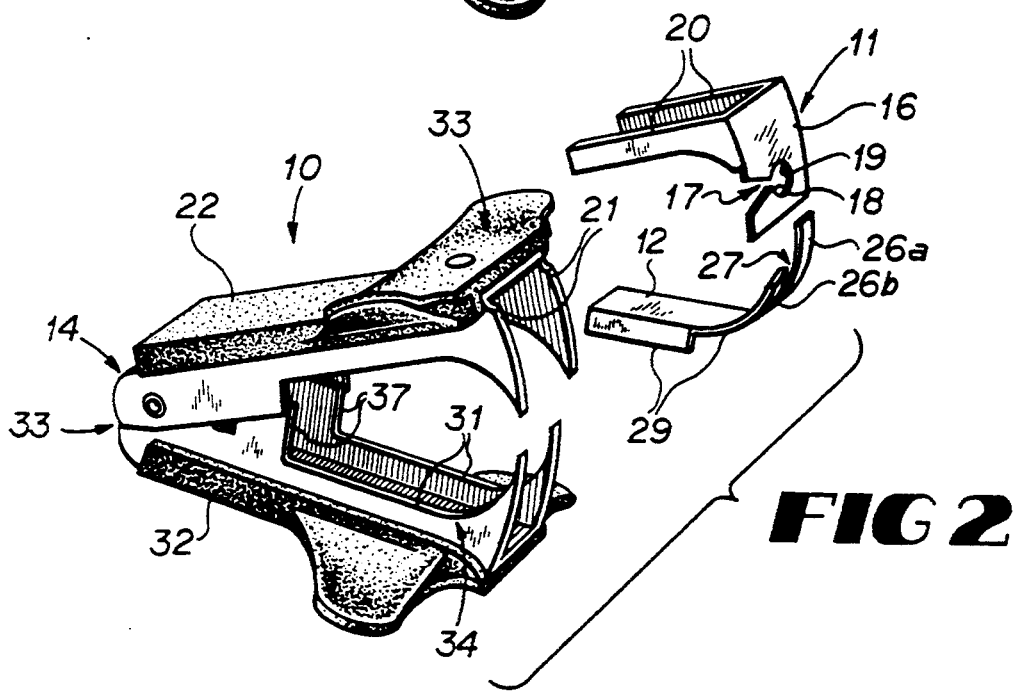
FIG. 2 is a perspective view of the assembly of the parasite remover shown in FIG. 1.

Referring now in more detail to the drawings, in which like numerals represent corresponding parts throughout the several views, FIGS. 1 and 2 are perspective views of the first embodiment of the parasite remover in accordance with the present invention. As shown, a parasite remover 10 comprises a holding plate 11, an engagement plate 12, and a commercially available staple remover 14. The staple remover 14 could be another similar clamping or pivoting device for accommodating the holding plate 11 and engagement plate 12 in a manner described hereinafter.

Holding plate 11 has a substantially flat portion 16 with a V-shape slot 17 therein located at the front of the staple remover 14. The V-shape slot 17 begins wide at an outer edge of front flat portion 16. The width of the V-shape slot 17 progressively decreases inwardly from the outer edge until reaching a restriction, or neck 18.

After the neck 18, a nearly circular inner aperture 19 is present.

For affixing the holding plate 11 to the staple remover 14, the holding plate 11 has clamping arms 20 which fold around from the front flat portion 16 so as to bind the holding plate 11 to the lateral side walls 21 of a first pivoting arm 22 of the staple remover 14. In the preferred embodiment, prior to placing the holding plate 11 in the staple remover 14 as shown in FIG. 2, the clamping arms 20 extend outwardly from the flat portion 16 at a slight inward angle, or an angle toward one another, so as to exert inward binding force as well as frictional force against the lateral side walls 21 of a first pivoting arm 22.

Engagement plate 12 has a pair of prongs 26a, 26b extending upwardly in e substantially curved manner from a flat portion of the engagement plate 12. As shown in FIG. 2, the distal end of the prong 26b is slightly higher than the distal end of the prong 26a, but the prongs 26a, 26b maintain similar curvature. The prongs 26a, 26b are spaced apart defining a slot 27 therebetween.

For affixing the engagement plate 12 to the staple remover 14, the engagement plate 12 has a pair of mounting flanges 29 extending from the flat portion to contact spaced, lateral side walls 31 of a second pivoting arm 32 of the staple remover 14. The flanges 29 exert inward binding force as well as frictional force against the outer surface of the lateral side walls 31 so as to mount, or clamp, the engagement plate 12 onto the lateral side walls 31 of the second pivoting arm 32. In the preferred embodiment, prior to placing the engagement plate 12 in the staple remover 14 as shown in FIG. 2, the flanges 29 extend downwardly from the flat portion 16 at a slight inward angle, or an angle toward one another, so as to exert the inward binding force as well as frictional force against the lateral side walls 31 of the second pivoting arm 32.

Side walls 31 further include stop shoulders 37 for engaging the first pivoting arm 22 when the pivoting arms 22, 32 are moved toward each other. The stop shoulders 37 serve the purpose of restricting, or confining, the movement of the pivoting arms 22, 32 toward each other so that the parasite is not undesirably squeezed or crushed. The pivoting arms 22, 32 are pivotally connected at pivoting end 33 and are spring-biased away from each other by a well known conventional spring-biasing mechanism (not shown). Holding plate 11 and engagement plate 12 are adapted to mount to the first pivoting arm 22 and the second pivoting arm 32, respectively, at what shall be referred to herein as the reciprocating ends 33 and 34 thereof.

Figure 3:
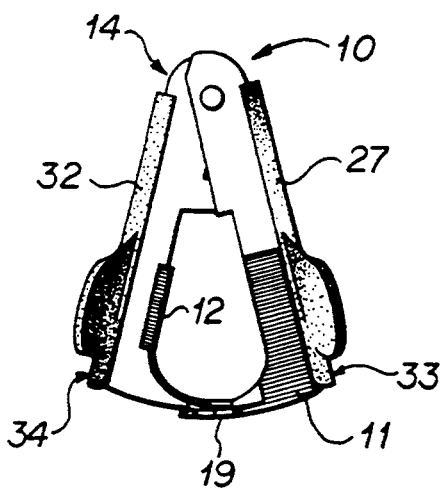
FIG. 3 is a side elevational view of the first embodiment illustrated in FIG. 1.

FIG. 3 shows a side elevational view of the parasite remover 10 of FIGS. 1 and 2. The parasite remover 10 is shown in FIG. 3 with the parasite remover 10 as well as the aperture 19 in an "open" position, wherein reciprocating ends 33, 34 of respective pivoting arms 22, 32 are spaced apart. When the parasite remover 10 is in an open position, the holding plate 11 and the prongs 26a, 26b of the engagement plate 12 only slightly overlap one another. In other words, the distal ends of the prongs 26a, 26b overlap only the bottom region of the flat portion 16 of the holding plate 11. This disposition causes the slot 17 of holding plate 11 and the slot 27, located between the prongs 26a, 26b, to intersect one another. Prong 26a being shorter than prong 26b prevents prong 26a from intersecting slot 17 with the parasite remover 10 in its open position. Thus, in the open position, the parasite remover 10 can be easily inserted between the parasite and the host skin, as discussed hereinafter. The inner edge of prong 26b can taper toward the inner edge of prong 26a, if desired, so that the slot 27 becomes progressively more narrow as it approaches plate 12 to direct the neck of the tick into the slot 27.

Figure 4:
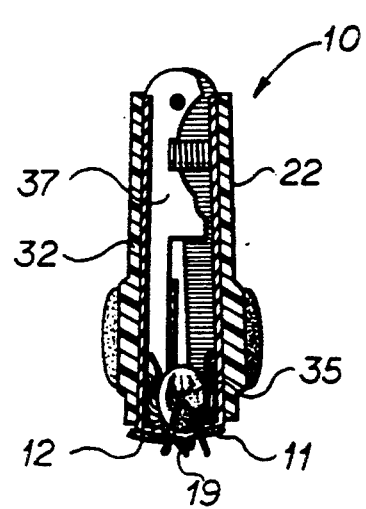
FIG. 4 is a cross sectional view of the first embodiment of FIG. 1 illustrating the parasite remover engaging a parasite.

FIG. 4 is a side elevational view of the parasite remover 10 shown in cross section engaging the parasite 35. To engage the parasite 35, the staple remover 14 is "closed," or that is, the reciprocating ends 33, 34 of respective pivoting arms 22, 32 are moved together. When pivoting arms 22, 32 are pivoted towards one another, the prongs 26a, 26b of engagement plate 12 move between the parasite 35 and take host skin, thereby slightly constraining aperture 19.

Worth noting is that when the staple remover 14 is in the closed position, the parasite 35 is substantially enclosed between the pivoting arms 22, 32 and is not squeezed or crushed thereby, due to stop shoulders 37. Thus, the parasite is prevented from expelling infectious fluids from within its body into the host through being squeezed.

Figures 5, 6:
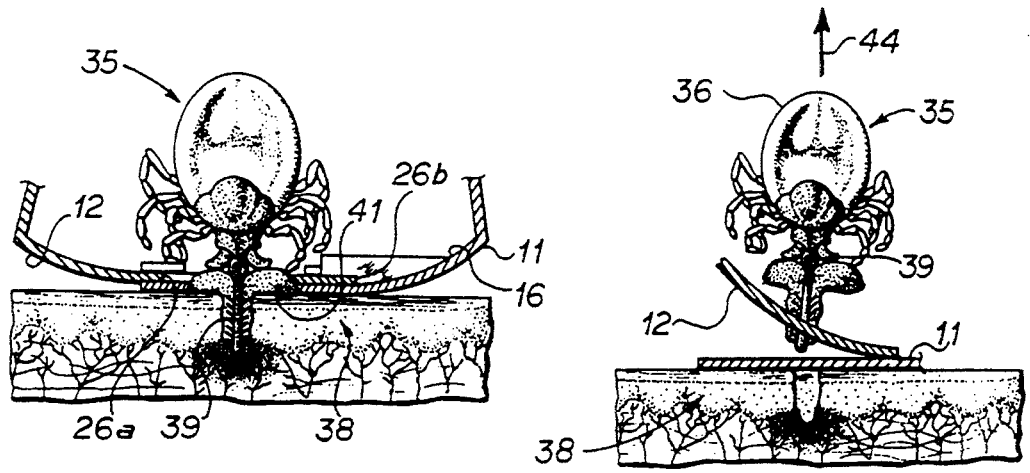
FIG. 5 is an exploded cross sectional view of a holding plate and an engagement plate of the first embodiment of FIG. 1 showing the holding plate inserted between a parasite's body and a host's skin.
FIG. 6 is a cross sectional view illustrating the operation of the holding plate and the engagement plate of FIG. 5.

FIG. 5 is a exploded cross sectional view of the holding plate 11 and the engagement plate 12 prior to engaging the parasite 35 between the parasite body and the host skin with the engagement plate 12. Initially, the parasite 35 is attached to the host skin 38 with the parasite mouth 39 inserted into the host skin 38 far enough for the end of the parasite mouth 39 to reach the blood stream of the host. Adherent cement 41 has been secreted by the parasite 35 in order to attach itself to the host skin 38.

In order to remove the parasite 35 with the parasite remover 10 in accordance with the present invention, the holding plate 11 is inserted between the parasite body and the host skin 38 with the parasite mouth 39 positioned within aperture 19 of the holding plate 11. The parasite mouth 39 is slid into the aperture 19 via the throughway defined by V-shaped slot 17. The second pivoting arm 32 is then pivoted toward the first pivoting arm 22 to force the engagement plate 12 to move toward the holding plate 11 with the distal ends of prongs 26a, 26b in abutment with the flat portion 16 of holding plate 11. This abutment ensures that the tips of prongs 26a, 26b scrape along the inner side of holding plate 11 near the aperture 19 so as to remove a part of the adherent cement 41 anchoring the parasite 35 to the host skin 38.

FIG. 6 is a cross sectional view illustrating the operation of the holding plate 11 and the engagement plate 12 of FIG. 5. The prongs 26a, 26b of the engagement plate 12 are curved away from the host skin 38. This curvature causes prongs 26a, 26b of the engagement plate 12 to engage the parasite body adjacent the parasite mouth 39 and force up, or apply upward pressure, to the parasite body 35 in a direction generally normal to the surface of the host skin 38, as indicated by an arrow 44. When the parasite 35 is extracted from the host skin 38 in this substantially normal direction, the parasite mouth 39 is moved along the length of the prongs 26a, 26b and is not bent and/or twisted. Hence, the parasite 35 is not irritated or dismembered, and the entire parasite mouth 39 is extracted from the host skin 38.

Figure 7:
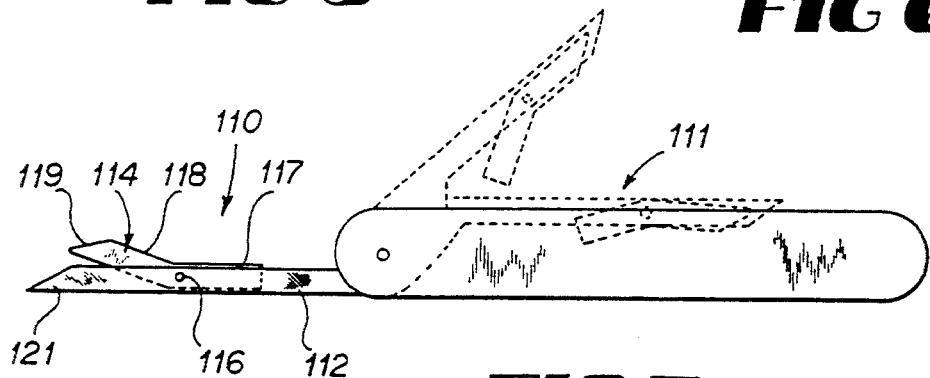
FIG. 7 is a side elevational view of a second embodiment in accordance with the present invention wherein the novel parasite remover is attached to a knife assembly.

FIG. 7 is a side elevational view of a second embodiment of the present invention, wherein a parasite remover 110 attached to a conventional pocket knife assembly 111 is used to remove a parasite 135 from host skin 138. Structurally, the parasite remover 110 has a handle arm 112 and a lever arm 114 pivotally mounted to the handle arm 112 at pivot 116. Lever arm 114 has a trigger arm 117 at one end and a host engaging prying arm 118 at the other end. The prying arm 118 is oriented at a nonlinear angle with respect to the trigger arm 117. The distal end 119 of prying arm 118 is angled to engage the surface of the host skin 38 and to apply downward force, or pressure, to the host skin 38, when the trigger arm 117 is moved upward by a user. In the same sense, when downward force is applied to the host skin 138 by the lever arm 114, all identical upward force is applied to the handle arm 112.

Figure 8:
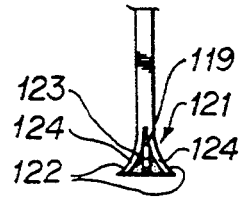
FIG. 8 is a front elevational view of the second embodiment shown in FIG. 7.

For engaging the parasite 135, the distal end 121 of handle arm 112 further includes a pair of spaced fork prongs 122 defining a slot 123 therebetween, as clearly shown in FIG. 8. The upper surfaces 124 of fork prongs 122 are flat and/or extremely dull so as to avoid cutting and/or pinching the parasite 135.

Figures 9, 10:
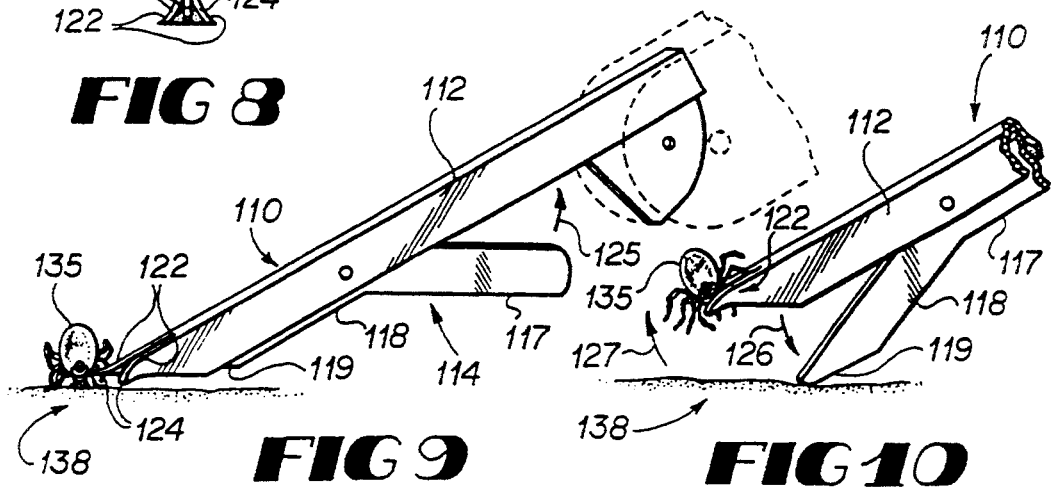
FIG. 9 is an exploded side view of the second embodiment of FIG. 7 just prior to removing a parasite from the skin of a host.
FIG. 10 is an exploded side view of the second embodiment of FIGS. 7 and 9 in the process of removing a parasite from the skin of a host.

FIG. 9 is an exploded side view of the second embodiment of FIG. 7 just prior to removing the parasite 135 from the host skin 138. Initially, the prying arm 118 of lever arm 114 is positioned in line with, or adjacent, the handle arm 112. The fork prongs 122 are spaced apart in order to allow the fork prongs 122 to be inserted between the parasite body 135 and the host skin 138, thereby straddling the parasite mouth 139.

FIG. 10 is an exploded side view of the second embodiment of FIGS. 7 and 9 in the process of removing the parasite 135 from the host skin of a host 138. By pivoting trigger arm 117 upwardly (in the direction denoted by an arrow 125 in FIG. 9) toward the handle arm 112, the prying arm 118 of the lever arm 114 pivots downwardly (in the direction denoted by in arrow 126 in FIG. 10) from the handle arm 112 into engagement with the host skin 138. Concurrently, the fork prongs 122 are forced upwardly away from the host skin 138 into engagement with the parasite body 135. This upward force pries the parasite 135 from the host skin 138 in a direction generally normal to the surface of the host skin 138, as indicated by an arrow 127.

It should be noted that the parasite remover 110, shown in FIGS. 7 through 10, can be easily manufactured from a variety of inexpensive, yet durable, materials, such as plastic, wood, or metal.

Figure 11:
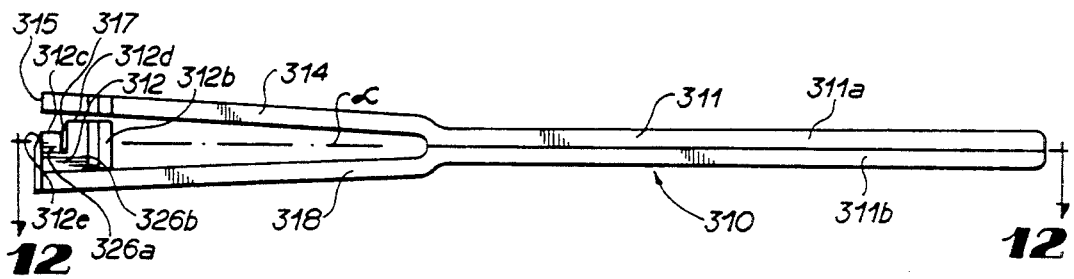
FIG. 11 is a plan view of a third embodiment, a parasite remover constructed in accordance with the present invention.
Figure 12:
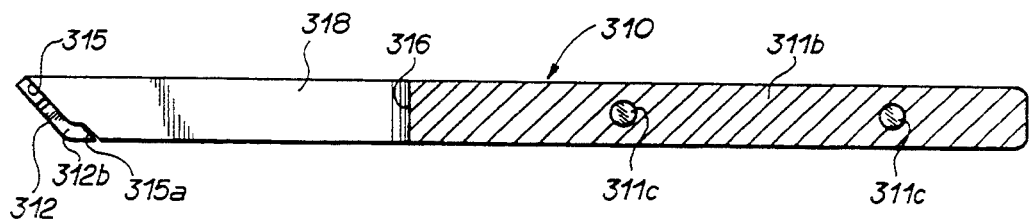
FIG. 12 is a cross sectional view taken substantially along line 12—12 in FIG. 11.
Figure 13:
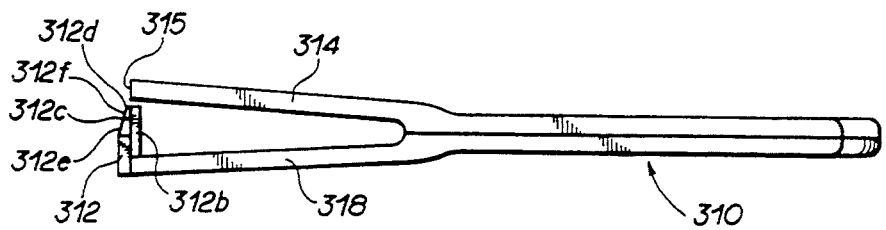
FIG. 13 is a front elevational view of the parasite remover depicted in FIG. 11.

In the third embodiment, depicted in FIGS. 11 through 13, the parasite remover 310 is shown as including a handle 311, one end portion of which is bifurcated to provide a pair of cantilever mounted, straight, opposed, normally diverging, spring yieldable arms 314 and 318 connected to arm 311 at pivot 316. The handle 311 and arms 314 and 318 form the tweezers of remover 310. Thus, arms 314 and 318 may be urged together by grasping the arms 314 and 318 between a thumb and forefinger and applying force simultaneously to both arms.

As seen best in FIGS. 12 and 13, the opposed distal ends of arms 314 and 318 are respectively angled at an acute angle of about 45° to a traverse plane passing along longitudinal axis a of the remover 310, to provide straight, inclined, opposed, complimentary, aligned bottom edges or surfaces, such as edge 315. The rear portions of both edges, such as edge 315, are notched as at numeral 315a.

Mounted in cantilever fashion by its proximal end portion to the bottom edge 315 and its notch 315a, is an inwardly extending, generally flat engagement plate 312. The rear portion of plate 312 is bent inwardly about a traverse bend to form a heel 312b so as to conform the plate 312 to the contour of the bottom edges, such as edge 315.

The distal end portion of plate 312 is bifurcated to provide a pair of opposed, spaced, parallel, sidewise extending, prongs or fingers 326a and 326b, the forwardmost prong 326a being shorter than the rear prong 326b. The lower portions of prongs or fingers 326a and 326b are both beveled so as to taper upwardly toward their respective straight transversely extending distal ends 312c and 312d.

The space between the adjacent prongs or fingers 326a and 326b form a straight slot 317, open at its distal end slot 317 terminating in a proximal end adjacent to, but spaced from arm 318. Slot 317 is of a uniform width which will accommodate the neck of the parasite so that the parallel prongs or fingers 326a and 326b extend on opposite sides of the neck as the parasite is received in slot 317.

The fingers or prongs 326a and 326b are of different lengths and protrude toward arm 314, the lower surface of fingers or prongs 326a, 326b being bevelled at an acute angle of about 45° so as to be inclined upwardly, providing bevelled surfaces 312e and 312f, tapering to the straight, narrow, transversely extending offset distal edges 312c and 312d of fingers or prongs 326a and 326b.

Prong 326b protrudes beyond edge 312c of the prong 326a so as to provide, with edge 312e, a V-shaped notch communicating with slot 317, for initially guiding the neck of the parasite into the mouth of slot 317.

When the parasite remover 310 is used, handle 311 is arranged at an acute angle of about 45° the surface of the skin of the host, so that the bottom of engagement plate 312 is against the host as the neck of the parasite is engaged, in much the same manner as in the preceding embodiments. In the initial phase of the removal of the parasite, the bevelled surfaces 312e and 312f, which are wedge shaped, enable the skin of a person to be pressed downwardly as the plate 312 is manipulated to arrange the neck of parasite in slot 317, so that the operator can, by progressively moving the two arms 314 and 318 together, cause the inner surface of arm 314 to move inwardly toward arm 318, sweeping over the upper surface of prongs 326a and 326b, lifting the parasite away from the skin of the host, as the bottom surface of arm 314 passes over prongs 326a and 326b urging the parasite body toward the closed end of slot 317. The lifting of the parasite body is caused by the wedge shape (in cross section) of the end portions of the prongs 326a and 32b. In other words, the leading edges 312c and 312d are knife-like edges having little thickness while, in the vicinity of the inner end of slot 317, the prongs are thicker. During this initial lifting of the parasite, the handle 311 and arms 314 and 318 are inclined at the acute angle of about 45° so that the plate 312 and bevelled portion are essentially flat against the skin of the host. When, however, the body of the parasite has been confined, and initially lifted, the handle 311 may then be lifted as the acute angle of the handle 311 is maintained or the handle can be tilted to reduce the incline, using the heel or bend 312b of plate 312 as a fulcrum about which the prongs 326a and 326b are tilted.

In construction of the parasite remover 310, it is preferable to produce tweezers in two complimentary parts which are later joined together. Hence, that portion of the tweezer on one side of line 12—12, including a handle half 311a and 314, can be cast as one unit and that portion of the tweezer on the other side, including a handle half 311b and arm 318, are cast as another unit. The two halves 311a and 311b of the handle 311 are later joined together for forming handle 311. In casting the units, protruding bosses 311c, shown in FIG. 12, are produced along the inner portion of handle half 311a, to be received in appropriate cavities (not shown), thereby permanently joining the two handle halves flat against each other. If desired, the engagement plate 312 can be integrally cast as a part of arm 318.

The features and principles of the present invention have been described with reference to several illustrative embodiments. However, it will be apparent to those skilled in the art that numerous modifications can be made to the illustrative embodiments without departing from the spirit of the present invention. All such modifications are intended to be included within the scope of the present invention as defined in the following claims.

The following is claimed:

1. A parasite remover for removing a parasite from the skin of a host comprising:
 a pair of opposed normally diverging arms secured together at their proximal ends, said arms having distal ends moveable toward and away from each other;
 an engagement plate on a distal end portion of one of said arms, said plate having a slot provided therein, said slot being open at one of its ends and closed another end for receiving a portion of said parasite between the body and mouth of the parasite when said plate is placed on said skin of said host and moved toward said portion of said parasite;
 said engagement plate having a configuration for urging said body of said parasite away from said skin of said host as said portion of said parasite is urged progressively into said slot;
 the other of said arms being moveable with respect to said one of said arms for producing relative motion between said plate and said parasite so as to cause said body of said parasite to be lifted by said engagement plate away from said skin of said host; and
 said other of said arms having a length in relation to said one of said arms so as to allow said other of said arms to sweep over said engagement plate when said arms are moved toward each other.

2. The parasite remover defined in claim 1 wherein said engagement plate has a pair of prongs having an upper surface and which define said slot protruding toward the distal end of said other of said arms, said distal end of said other of said arms having a surface conforming to the shape of said upper surface of said prongs so as to pass over said upper surface when said arms are urged together for confining said body of said parasite between said arms.

3. The parasite remover defined in claim 2 wherein said upper surface is essentially flat and said engagement plate is disposed on said one of said arms at an acute angle to said one of said arms, said surface of said distal end of said other of said arms being disposed at said acute angle.

4. The parasite remover defined in claim 1 wherein said slot opens toward said other of said arms.

5. The parasite remover defined in claim 1 wherein said engagement plate has a lower surface which converges toward said upper surface in a direction toward said other of said arms.

6. The parasite remover defined in claim 5 wherein said configuration of said engagement plate forms a wedge shape, tapering toward said other of said arms.

* * * * *